(12) United States Patent
Zaicenko et al.

(10) Patent No.: US 12,081,393 B2
(45) Date of Patent: Sep. 3, 2024

(54) VIRTUAL SMART NETWORK INTERFACE CARD FOR EDGE DEVICE

(71) Applicant: Oracle International Corporation, Redwood Shores, CA (US)

(72) Inventors: Kirils Zaicenko, Cumming, GA (US); David Dale Becker, Seattle, WA (US); Maxim Baturin, Sammamish, WA (US); Tadeusz Jakub Dul, Redmond, WA (US)

(73) Assignee: Oracle International Corporation, Redwood Shores, CA (US)

( * ) Notice: Subject to any disclaimer, the term of this patent is extended or adjusted under 35 U.S.C. 154(b) by 418 days.

(21) Appl. No.: 17/569,470

(22) Filed: Jan. 5, 2022

(65) Prior Publication Data

US 2022/0329457 A1 Oct. 13, 2022

Related U.S. Application Data

(60) Provisional application No. 63/173,244, filed on Apr. 9, 2021.

(51) Int. Cl.
*G06F 3/06* (2006.01)
*G06F 8/61* (2018.01)
(Continued)

(52) U.S. Cl.
CPC ........ *H04L 41/0806* (2013.01); *G06F 3/0604* (2013.01); *G06F 3/0622* (2013.01);
(Continued)

(58) Field of Classification Search
CPC ............... H04L 41/0806; H04L 9/0897; H04L 12/4641; H04L 63/0471; H04L 63/0478;
(Continued)

(56) References Cited

U.S. PATENT DOCUMENTS

| 8,613,070 B1 | 12/2013 | Borzycki et al. |
| 10,404,613 B1 | 9/2019 | Brooker et al. |

(Continued)

OTHER PUBLICATIONS

U.S. Appl. No. 17/531,566, Notice of Allowance mailed on Mar. 21, 2023, 10 pages.

(Continued)

*Primary Examiner* — Kent Krueger
(74) *Attorney, Agent, or Firm* — Kilpatrick, Townsend & Stockton, LLP

(57) ABSTRACT

Techniques are described for implementing a virtual smart network interface card to facilitate data transmission in an edge device providing cloud-computing operations. An edge device can implement a private virtual network that includes a private virtual network data plane. The edge device can execute a virtual machine to be connected to the private virtual network. To establish the connection, the edge device can generate a virtual network interface that includes a first endpoint and a second endpoint and is hosted within the private virtual network data plane. The edge device can associate the first endpoint with the virtual machine and associate the second endpoint with an orchestration module of the private virtual network data plane. The virtual machine can then send a data packet to the orchestration module via the virtual network interface.

20 Claims, 12 Drawing Sheets

(51) Int. Cl.

| | |
|---|---|
| *G06F 8/658* | (2018.01) |
| *G06F 9/4401* | (2018.01) |
| *G06F 9/455* | (2018.01) |
| *G06F 9/50* | (2006.01) |
| *G06F 11/14* | (2006.01) |
| *H04L 9/08* | (2006.01) |
| *H04L 9/40* | (2022.01) |
| *H04L 12/46* | (2006.01) |
| *H04L 41/0806* | (2022.01) |
| *H04L 67/10* | (2022.01) |

(52) U.S. Cl.
CPC .......... *G06F 3/0655* (2013.01); *G06F 3/0659* (2013.01); *G06F 3/067* (2013.01); *G06F 3/0679* (2013.01); *G06F 8/61* (2013.01); *G06F 8/658* (2018.02); *G06F 9/4406* (2013.01); *G06F 9/45558* (2013.01); *G06F 9/505* (2013.01); *G06F 9/5055* (2013.01); *G06F 9/5077* (2013.01); *G06F 9/5088* (2013.01); *G06F 11/1451* (2013.01); *G06F 11/1469* (2013.01); *H04L 9/0897* (2013.01); *H04L 12/4641* (2013.01); *H04L 63/0471* (2013.01); *H04L 63/0478* (2013.01); *H04L 63/0485* (2013.01); *H04L 63/06* (2013.01); *H04L 63/0876* (2013.01); *H04L 63/162* (2013.01); *H04L 63/20* (2013.01); *H04L 67/10* (2013.01); *G06F 2009/45562* (2013.01); *G06F 2009/45587* (2013.01); *G06F 2009/45595* (2013.01); *G06F 2201/84* (2013.01)

(58) Field of Classification Search
CPC . H04L 63/0485; H04L 63/06; H04L 63/0876; H04L 63/162; H04L 63/20; H04L 67/10; G06F 8/658; G06F 8/61; G06F 3/0604; G06F 3/0622; G06F 3/0655; G06F 3/0659; G06F 3/067; G06F 3/0679; G06F 9/4406; G06F 9/45558; G06F 9/505; G06F 9/5055; G06F 9/5077; G06F 9/5088; G06F 2009/45562; G06F 2009/45587; G06F 2009/45595; G06F 11/1451; G06F 11/1469; G06F 2201/84

See application file for complete search history.

(56) References Cited

U.S. PATENT DOCUMENTS

| | | |
|---|---|---|
| 11,683,220 B2 | 6/2023 | Maheshwari et al. |
| 11,777,796 B2 | 10/2023 | Baturin |
| 2013/0332927 A1 | 12/2013 | Tang et al. |
| 2015/0378753 A1 | 12/2015 | Phillips et al. |
| 2018/0103088 A1 | 4/2018 | Blainey et al. |
| 2019/0007339 A1 | 1/2019 | Bao et al. |
| 2019/0036687 A1 | 1/2019 | Raza et al. |
| 2021/0132976 A1* | 5/2021 | Chandrappa ........ G06F 9/45558 |
| 2021/0168203 A1* | 6/2021 | Parulkar ................ H04L 67/60 |
| 2023/0011628 A1 | 1/2023 | Hurley et al. |
| 2023/0049501 A1 | 2/2023 | Xu et al. |

OTHER PUBLICATIONS

U.S. Appl. No. 17/565,337, Notice of Allowance mailed on May 11, 2023, 11 pages.
U.S. Appl. No. 18/296,348, Notice of Allowance mailed on Dec. 20, 2023, 5 pages.
U.S. Appl. No. 18/296,348, Non-Final Office Action mailed on Nov. 7, 2023, 10 pages.
U.S. Appl. No. 18/330,227, Notice of Allowance mailed on Mar. 13, 2024, 14 pages.
Li, Edge Computing, A Compensation Method for Cloud Computing on Smart Grid, The University of New South Wales Sydney, 2020, 95 pages.

* cited by examiner

VIRTUAL SMART NETWORK INTERFACE CARD FOR EDGE DEVICE

CROSS-REFERENCE TO RELATED APPLICATIONS

This non-provisional application claims priority to U.S. Patent Application No. 63/173,244, filed on Apr. 9, 2021, entitled "Cloud Computing Edge Computing Device (Rover)," the disclosure of which is herein incorporated by reference in its entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components.

BRIEF SUMMARY

Embodiments of the present disclosure relate to providing enhanced networking functionality for devices providing cloud computing or other distributed computing services at an "edge" location. In particular, a distributed computing cluster can be composed of a plurality of cloud-computing edge devices that collectively provide cloud-computing infrastructure and related services outside a traditional cloud environment. Some embodiments provide a method, a cloud-computing edge device, and a computer-readable medium that implement a private virtual network data plane on an edge device. The private virtual network data plane may include a virtual smart network interface card (virtual smart NIC), which may be responsible for providing networking functionality for one or more virtual machines hosted on the cloud-computing edge device, similar to a "bump in the wire" physical device provided in traditional cloud-computing infrastructure. However, because the edge devices may be located outside of the secure physical environment of traditional cloud-computing resources (e.g., secure data centers), embodiments of the present disclosure provide techniques for providing smart network functionality for an edge device that cannot implement a physical smart NIC.

One embodiment is directed to a method performed by a cloud-computing edge device. The method may include implementing a private virtual network. The private virtual network can include a private virtual network data plane hosted within an execution environment of the cloud-computing edge device. For example, the cloud-computing edge device may include a containerization engine that can orchestrate one or more containers to host processes and modules that form the private virtual network data plane. The method can also include executing a virtual machine on the cloud-computing edge device. The method can further include generating a virtual network interface hosted within the private virtual network data plane. The virtual network interface can include a first endpoint and a second endpoint. The endpoints may be virtual networking components, for instance a pair of virtual Ethernet interfaces (e.g., Linux virtual Ethernet (veth) devices). The method can also include establishing a communication connection between the virtual machine and a component of the private virtual network data plane. Establishing the communication connection can include associating the first endpoint with the virtual machine and associating the second endpoint with an orchestration module of the private virtual network data plane. Associating the first and second endpoints can include attaching or otherwise adding the endpoint to a networking namespace accessible by the corresponding component. The method can also include sending a data packet from the virtual machine to the orchestration module via the virtual network interface.

In some embodiments, the method further includes executing a second virtual machine on the cloud-computing edge device, generating a second virtual network interface, and establishing an additional communication connection between the second virtual machine and the orchestration module of the private virtual network data plane. The second virtual network interface can include a third endpoint and a fourth endpoint. The cloud-computing edge device can establish the communication connection by associating the third endpoint with the second virtual machine and associating the fourth endpoint with the orchestration module. As with the first and second endpoints, associating the third and fourth endpoints can include attaching or otherwise adding the endpoints to the networking namespaces accessible by the corresponding components.

In some embodiments, the data packet may be sent to various destinations within the distributed computing cluster. The orchestration module can include appropriate routing information (e.g., routing tables) to forward the data packet to its destination. The data packet may be sent from the first virtual machine to the second virtual machine using the first virtual network interface and the second virtual network interface. The data packet may be forwarded to an external device communicatively connected to the cloud-computing edge device through a public network (e.g., the internet). The private virtual network data plane can include an internet gateway that can provide a networking interface to the public network. The data packet may be forwarded to an additional cloud-computing edge device in the distributed computing cluster. The additional cloud-computing edge device may be communicatively connected to the cloud-computing edge device through a substrate network.

In some embodiments, the method can further include executing a command proxy module configured to modify a first networking namespace of a host operating system executing on the cloud-computing edge device. A private virtual network control plane may not have sufficient permissions to modify the first networking namespace when associating the first endpoint of the virtual network interface with the virtual machine. The command proxy module may be provided with appropriate permissions to make such modification. The method can also include receiving a request to create the virtual network interface. The request can include a networking command (e.g., a command to create or add a networking device to a namespace). The request may be generated by the private virtual network control plane and sent to the private virtual network data plane. The method can also include sending the networking command to the command proxy module and generating the virtual network interface within the first networking namespace. Generating the virtual network interface may be done by executing the networking command. The first endpoint of the virtual network interface can be associated with the first networking namespace of the host operating system and the second endpoint can be associated with a second networking namespace of the orchestration module.

Another embodiment is directed to a cloud-computing edge device configured with one or more processors and one or more memories storing computer-executable instructions that, when executed by the one or more processors, cause the cloud-computing edge device to perform the method described in the preceding paragraphs.

Still another embodiment is directed to a non-transitory computer-readable medium storing computer-executable instructions that, when executed by one or more processors of a cloud-computing edge device, cause the cloud-computing edge device to perform the methods disclosed herein.

DETAILED DESCRIPTION

Introduction

Figure 1:
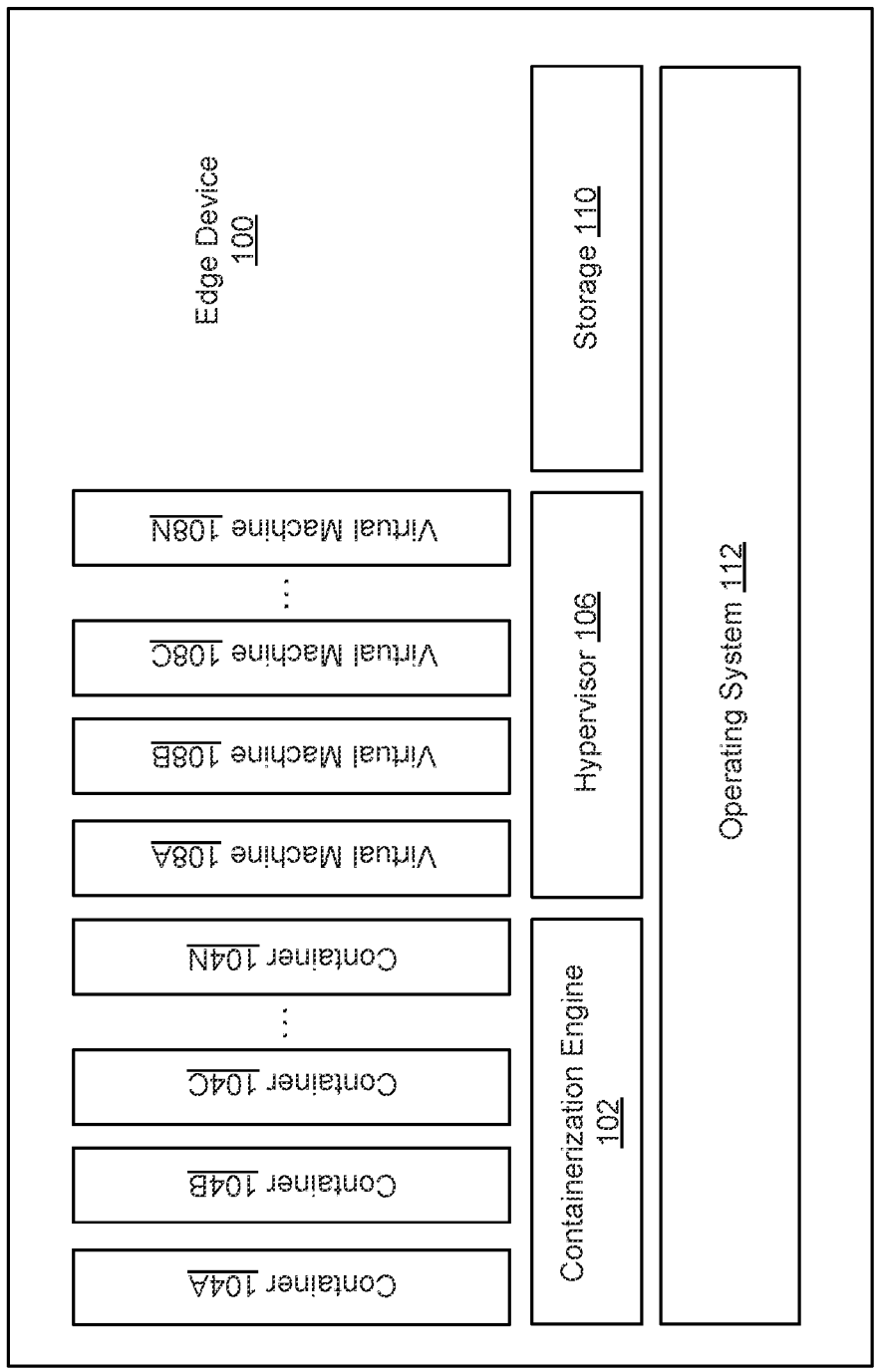
FIG. 1 is a block diagram of an example high-level architecture for a cloud infrastructure edge computing device, according to at least one embodiment.

In some examples, a cloud-integrated edge service (e.g., implemented in an edge computing device) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud edge device" or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to service(s) 104A, 104B, 104C, to 104N, collectively referred to as "service(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) and/or a hardware-based Virtual Machine (QEMU). Although storage 110 is represented as a separate component from the container(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
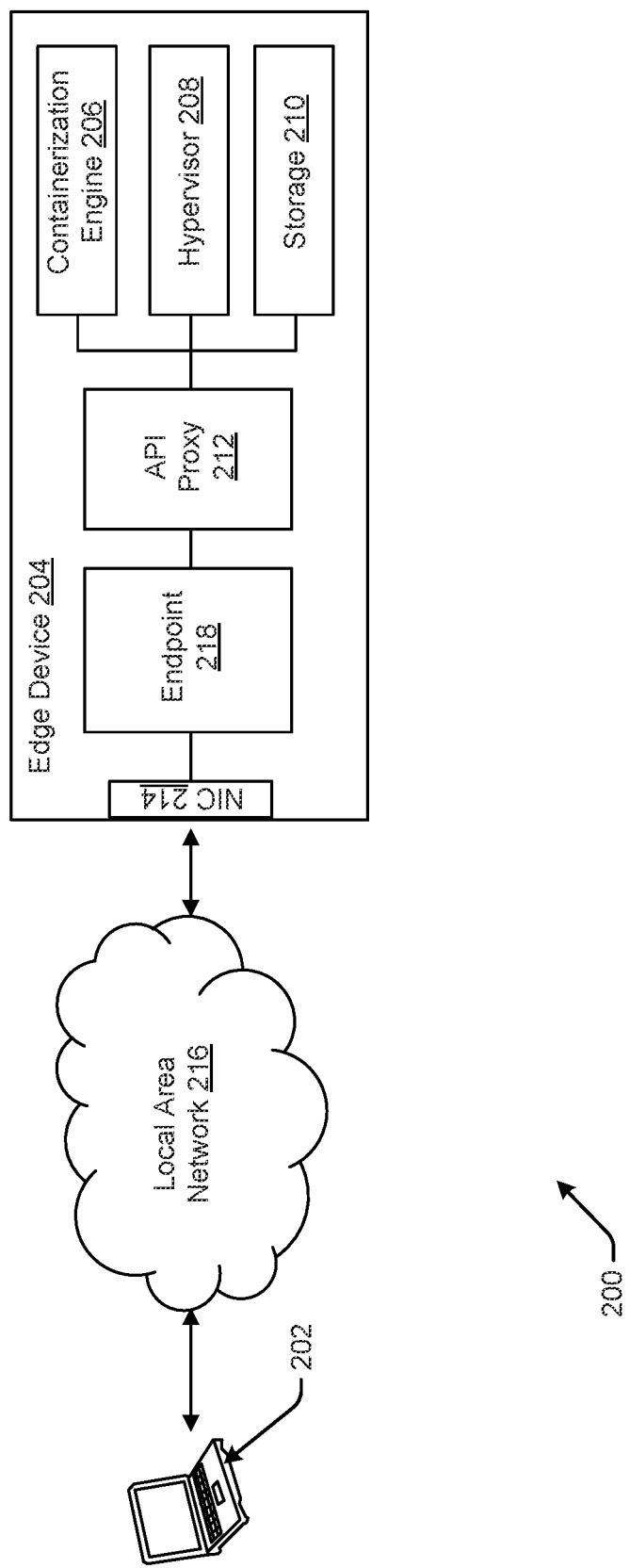
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The network interface card 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API Proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
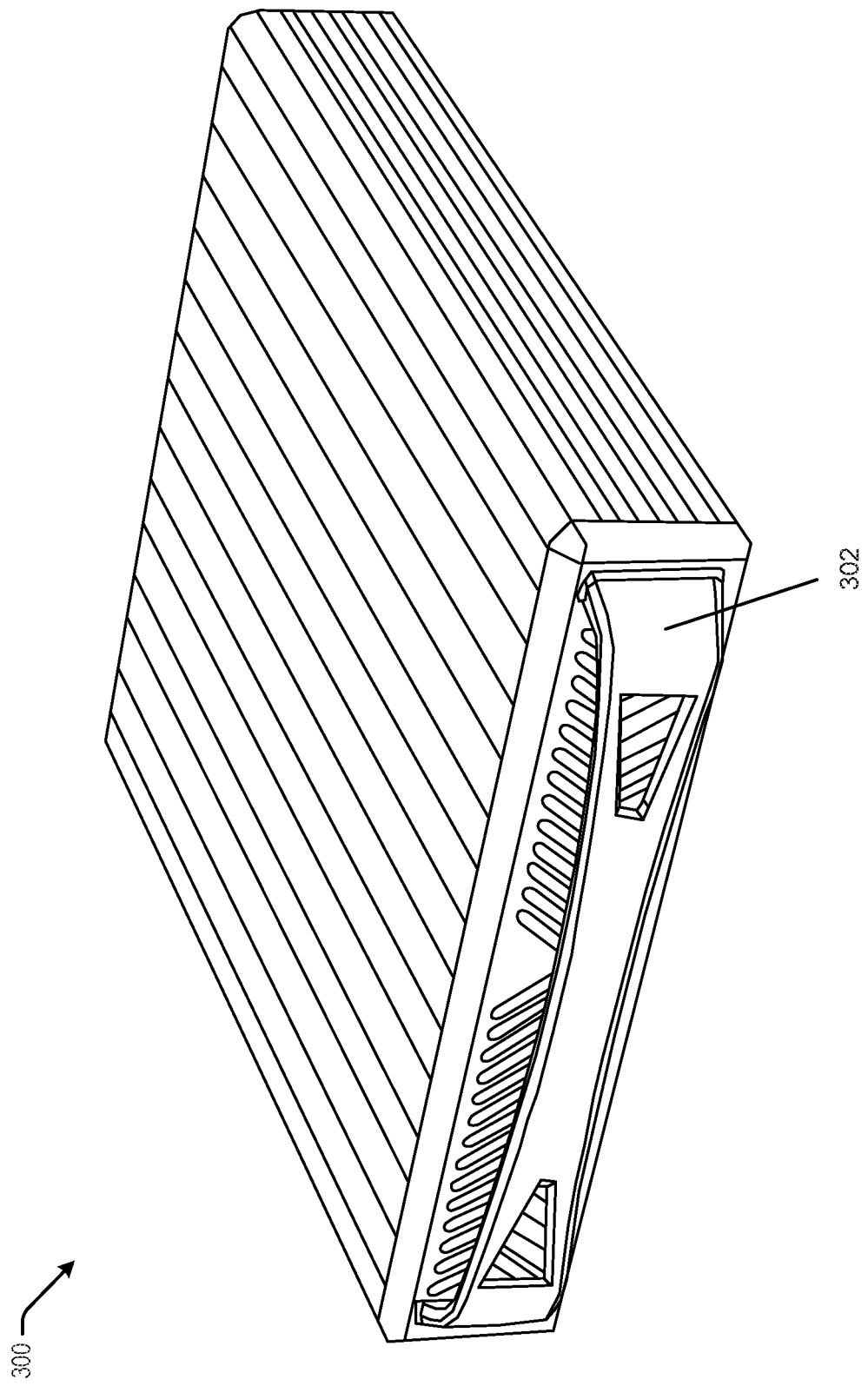
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure may not be possible to open. However, in some cases, it might be possible, but it would require extreme measures.

Figure 4:
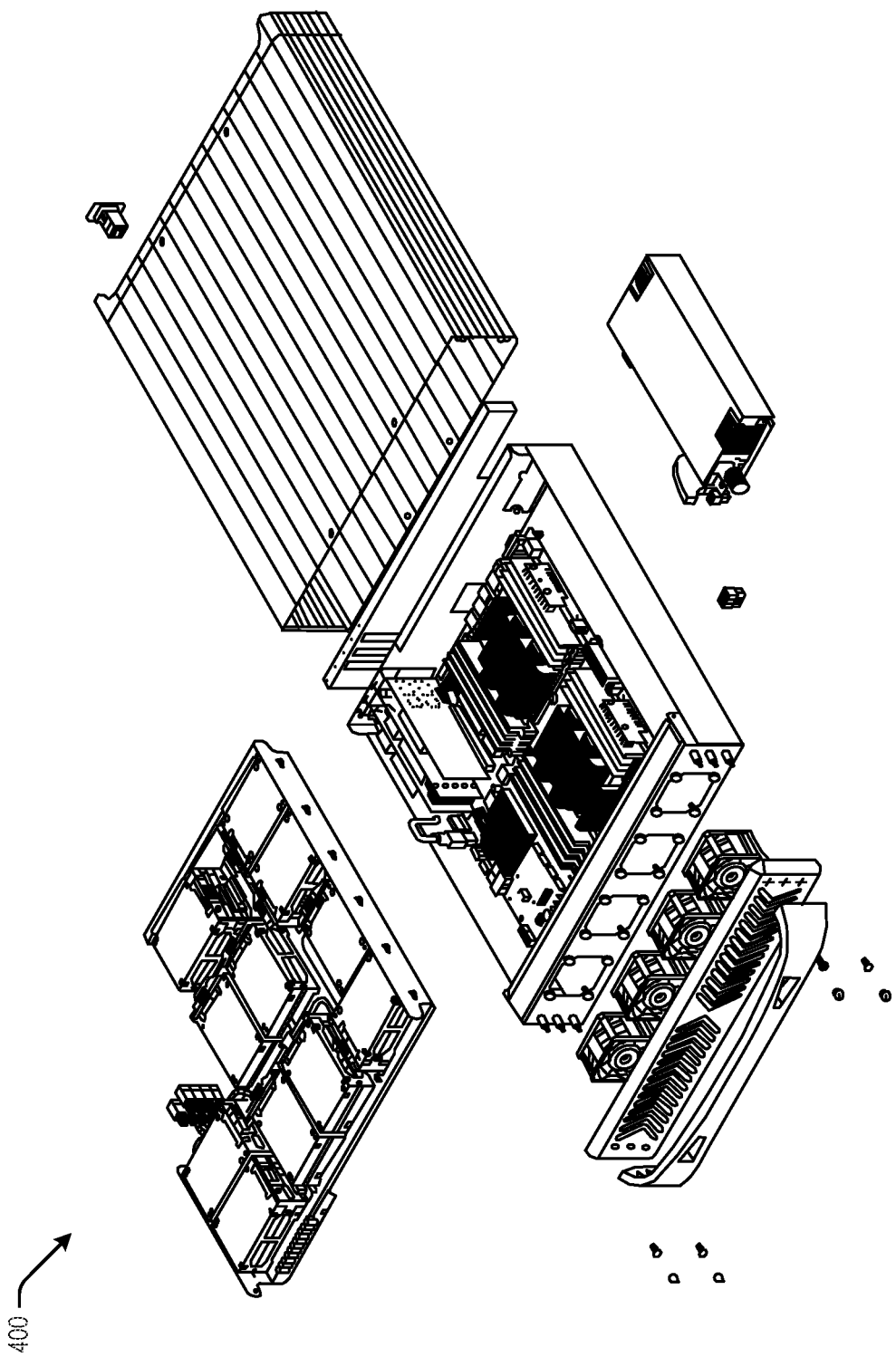
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
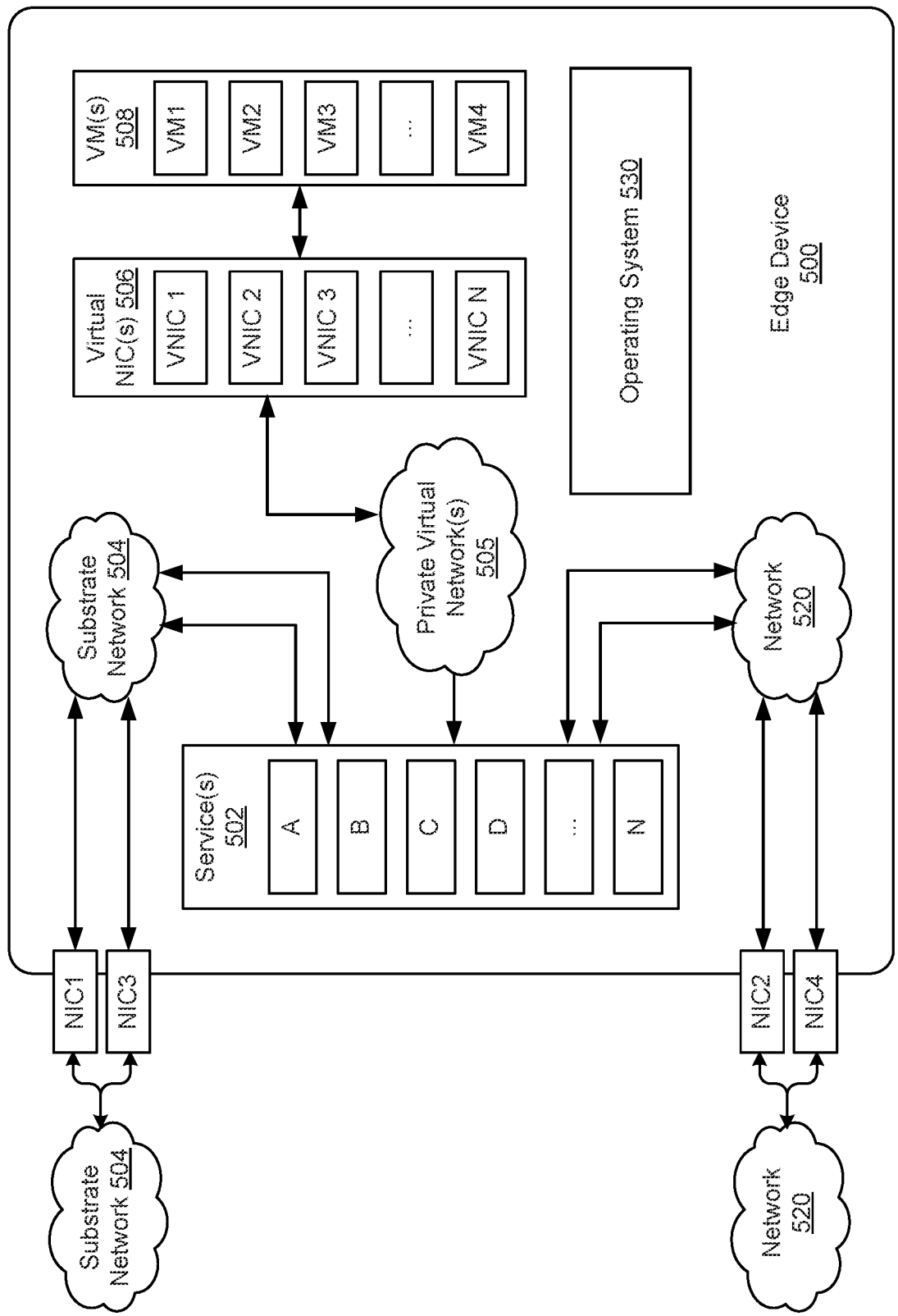
FIG. 5 is a block diagram of an example computer architecture of a cloud infrastructure edge computing device, according to at least one embodiment.

FIG. 5 is a block diagram of an example computer architecture 500 of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations outside of cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage (a product of Red Hat, Inc.)), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network(s) 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snapshots and copying block volumes. VM images and VM block volumes can be Ceph block devices. In some embodiments, the VM(s) implementing the distributed data storage platform will use system reserved resources (e.g., 8 CPU cores, some of the total number of CPUs available on the edge device 500). For example in order to provision a boot volume, a block device image may be copied to a boot volume of the block device. The distributed data storage platform may use block devices include multiple nodes for redundancy. If some node fails then the block device can continue to operate. In some embodiments, the distributed data storage platform (e.g., Ceph), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snapshot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer.

In some embodiments, the edge device 300 may provide any suitable number of virtual networks (e.g., private virtual network(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 500, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
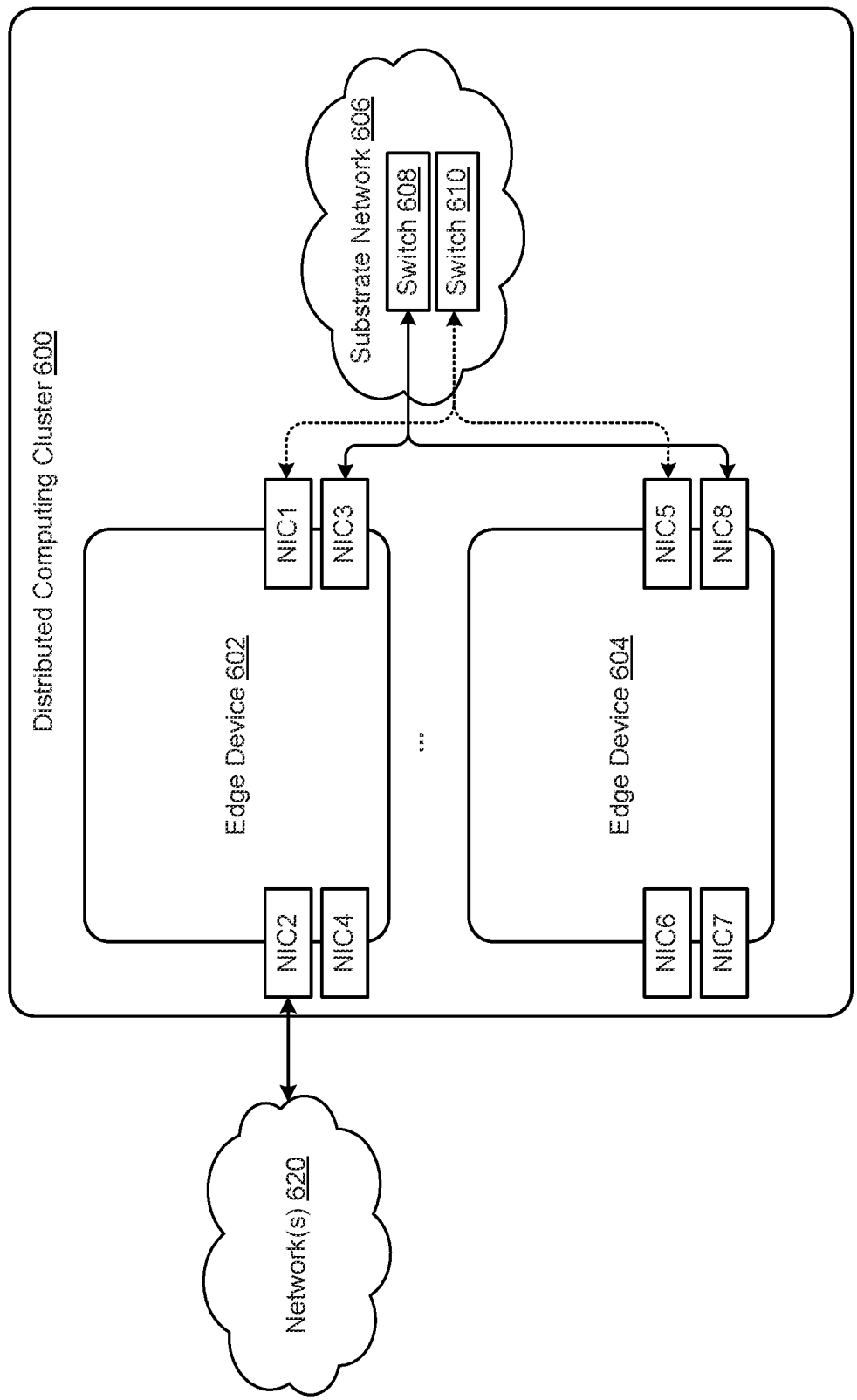
FIG. 6 is a block diagram depicting a distributed computing cluster that includes one or more edge computing devices, according to at least one embodiment.

FIG. 6 is a block diagram depicting a distributed computing cluster 400 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network(s) 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 400. In other embodiments, the user can configured the number and topology of the edge devices of the distributed computing cluster 600.

Figure 7:
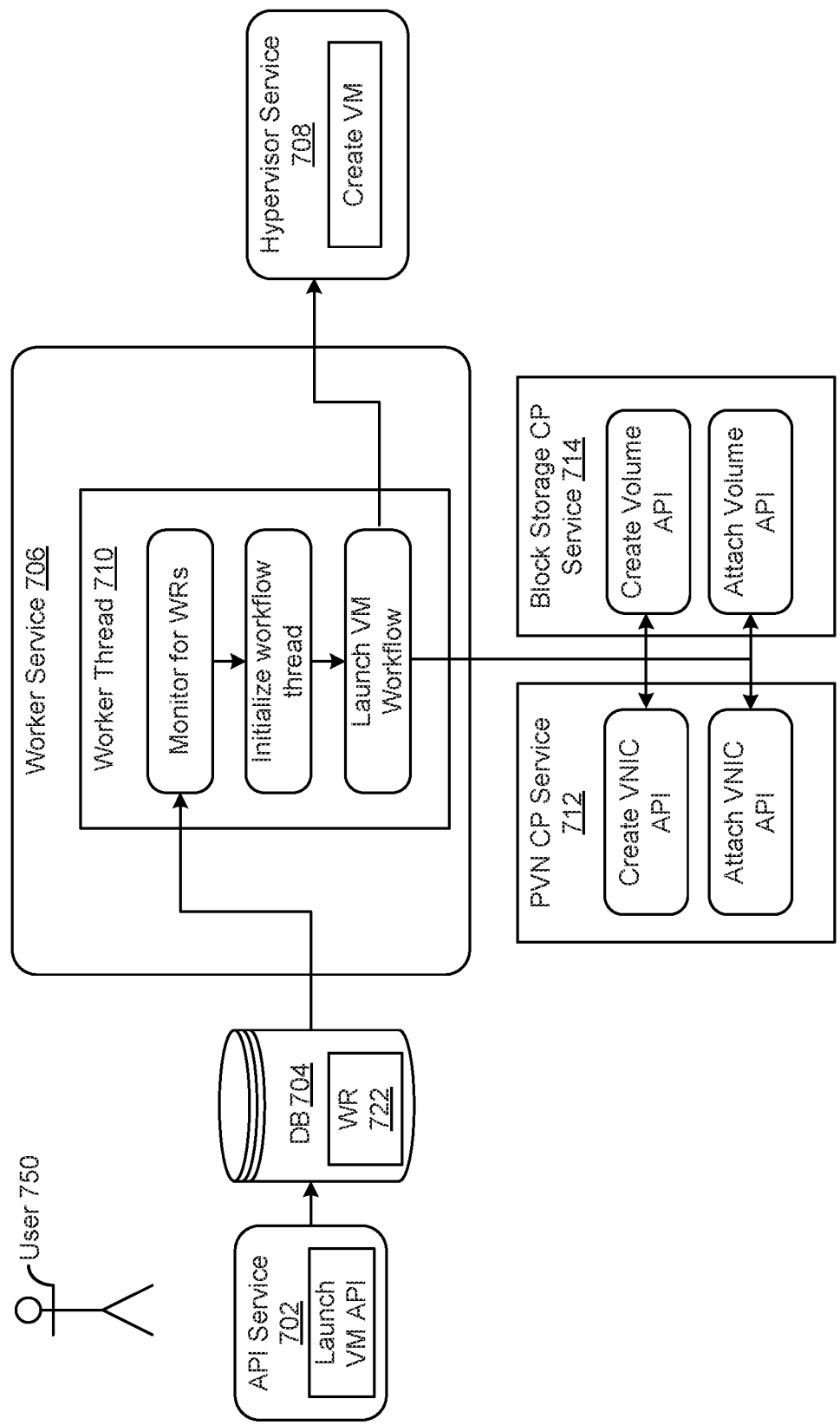
FIG. 7 is a block diagram depicting a control plane and flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database 704, service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device 202 of FIG. 2) to access a user interface with which he can make various selections indicating a desire to launch a VM. The user input may be received by the API service 702 (an example of the compute CP service of FIG. 5) which may generate a work request (e.g., WR 722) and utilize a predefined Launch VM API to store the work request in a distributed database (e.g., DB 704). In some embodiments, the DB 704 may be a computing cluster which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Service 706 (e.g., also an example of the compute CP service of FIG. 5) may be configured to execute one or more worker processes (e.g., computing thread 710). Some of these worker processes may be configured by the service 706 at any suitable time to execute a continuous and/or ongoing predefined workflow. By way of example, the service 706 may configure one or more worker threads (e.g., including computing thread 710) to monitor the DB 704 for new work requests (e.g., WR 722). The computing thread 710 may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 504 of FIG. 5) to a workflow service (not depicted). The workflow service may be configured to identify, from one or more predefined workflows, one that corresponds to launching a VM, and therefore, to the work request 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

Virtual Smart NIC

As discussed above, the edge devices may provide one or more networks within a distributed computing cluster (e.g., distributed computing cluster 600 of FIG. 6). The networks can include physical networks and/or virtual networks (e.g., private virtual network(s) 505 network 520, substrate network 504, etc.) within and/or between one or more edge devices (e.g., edge device 500 of FIG. 5). In addition to the network interface cards and virtual network interface cards (e.g., NIC 214 of FIG. 2, virtual NICs 506, etc.) implemented by the edge devices, an edge device may also host a virtual "smart" NIC (VSNIC) that can provide additional networking functionality within the distributed computing cluster. In particular, a VSNIC may be configured to provide any suitable number of virtual networking interfaces accessible to processes and/or modules executing on an edge device as well as modules to provide cloud networking functionality, including internet gateway, domain name service (DNS), network address translation (NAT), network time protocol (NTP), firewall, one or more subnets, security policies, metric tracking, throttling, secondary VNICs, and other similar functions.

A VSNIC may provide functionality similar to a "bump in the wire" networking device (e.g., a physical smart NIC). A bump in the wire device can provide enhanced networking functions for networking traffic passing through the device, for example tunneling for a firewall, tunneling to other smart NICs, enforcing firewall rules, and the like. Unlike a physical bump in the wire device, which may be connected to one or more physical NICs of an edge device, a VSNIC may be implemented as an instance of a private virtual network data plane within the edge device, such that enhanced network functionality may be hosted within the software environment of the edge device. Such an implementation is advantageous in situations where the physical security of the edge devices within the distributed computing cluster may be insufficient to protect access to a physical smart NIC device (e.g., deployments of clusters of edge devices in remote locations). In addition, the VSNIC may allow the distributed computing cluster to provide functionality equivalent to a cloud-based infrastructure service model, even when the cluster is disconnected from the internet and without requiring significant, if any, modifications to how customers interact with the cloud infrastructures services.

Figure 8:
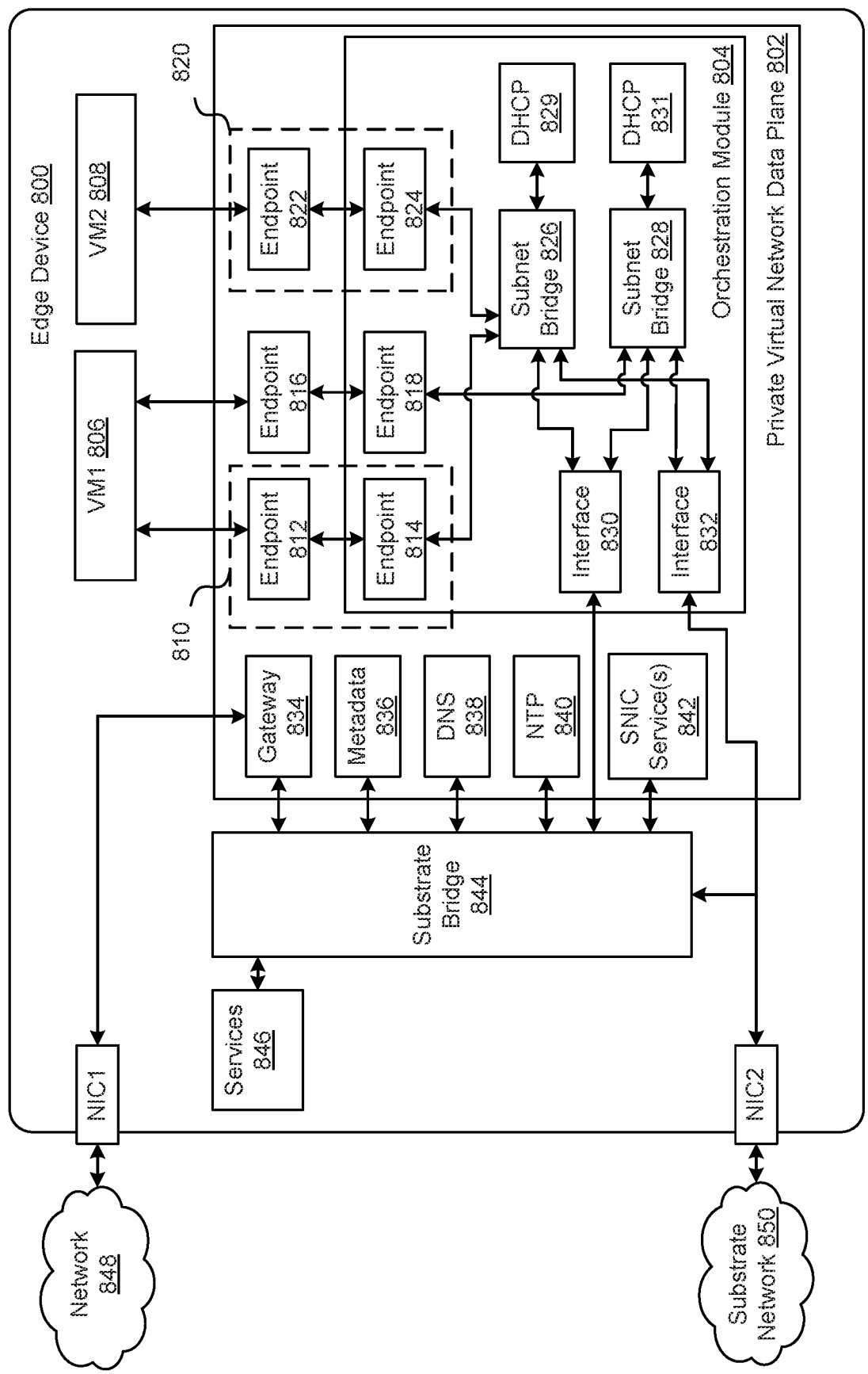
FIG. 8 is a block diagram depicting an edge device that includes a private virtual network data plane, according to at least one embodiment.

FIG. 8 is a block diagram depicting an edge device 800 that includes a private virtual network (PVN) data plane 802. The PVN data plane 802 may represent a virtual smart network interface card (VSNIC) and may be an example of the virtual NIC(s) 506 of FIG. 5. The edge device 800 may be similar to other edge devices described herein, including edge device 204 of FIG. 2 and edge device 500 of FIG. 5. The PVN data plane 802 may be a data plane corresponding to the PVN(s) 505 of FIG. 5. As a data plane, the PVN data plane 802 may include a collection of software (e.g., processes, threads, jobs, applications, modules, and the like) configured to support the data operations (e.g., sending, receiving, negotiating connections, etc.) for the PVN(s). The PVN(s) may include networks of one or more virtual machines (e.g., VM1 806, VM2 808, each an example of the VM(s) 508 of FIG. 5), one or more containers, one or more services (e.g., services 846, an example of the service(s) 502 of FIG. 5) and/or other processes or services executing on the edge device 800. The PVN(s) may also interface with additional networks, including network 848 (e.g., a client network or public network, network 520 of FIG. 5) and network 850 (e.g., substrate network 504 of FIG. 5). Physical network interfaces (e.g., NIC1, NIC2) of the edge device 800 may be similar to NIC 214 of FIG. 2 or other physical NICs described herein (e.g., NIC1-NIC4 of FIG. 5) and may provide one or more physical network connections (e.g., RJ45, QSFP28, etc.).

The PVN data plane 802 may execute in one or more containers (e.g., containers 104A-104C of FIG. 1) hosted by the edge device 800. For example, networking services including gateway module 834, metadata service 836, domain name system (DNS) service 838, network time protocol (NTP) service 840, and other smart network interface card (SNIC) service(s) 842 may each execute as its own container. The containers may utilize a separate networking namespace for each container. As used herein, networking namespace refers to an instance (e.g., a logical copy) of the network stack of the host device. The network stack in turn may refer to the configuration of all associated networking functionality of host device for the relevant networking layers (e.g., physical, networking, transport, application, etc.), including port configurations, routing tables, addressing, networking interfaces, virtual networking devices (e.g., bridges, virtual local area networks (VLANs), virtual Ethernet ports, other interfaces, etc.), drivers, protocols, protocol configuration, and the like. Thus, the containers of PVN data plane 802 may provide distinct networking namespaces for different portions of the PVN data plane 802. The execution of the PVN data plane 802 components may be supported by the host operating system (e.g., operating system 112 of FIG. 1), containerization engine (e.g., containerization engine 102 of FIG. 1), and/or hypervisor (e.g., hypervisor 106 of FIG. 1).

In some embodiments, some of the components of the PVN data plane 802 may share the networking namespace of the PVN data plane 802. These components can include an orchestration module 804. The orchestration module 804 may be configured to provide appropriate network interfaces, subnets, routing tables, firewall, NAT, and/or other networking functionality for the PVN data plane 802. The orchestration module 804 may include an application programming interface (API) for the PVN data plane 802. In some embodiments, the orchestration module 804 may be hosted in a container that can provide a networking namespace for the orchestration module 804. The networking namespace for the orchestration module 804 may be different from a networking namespace of the host operating system. In this way, the orchestration module 804 may include a different configuration of networking interfaces, virtual devices, routing tables, and/or addresses from the host operating system or other containers of the PVN data plane 802.

In some examples, the PVN data plane 802 can include virtual network interfaces configured to connect one or more virtual machines of the edge device 800 to a PVN. As shown in FIG. 8, the virtual network interfaces can include virtual network interface 810 and virtual network interface 820. The virtual network interfaces may include endpoints of a virtual networking device. For example, network interface 810 can include endpoint 812 and endpoint 814. Endpoints 812 and 814 may be virtual network devices (e.g., Linux virtual Ethernet (veth) devices). A virtual network device pair may be linked so that network traffic (e.g., packets, frames, etc.) sent to one virtual network device (e.g., endpoint 812, a Linux Ethernet device) is received at the paired device (e.g., endpoint 814, another Linux Ethernet device), similar to data transmitted over a physical Ethernet wire. Thus, endpoints 812 and 814 may form a virtual wire within the PVN data plane 802 from VM1 806 to the subnet bridge 826. Similarly, virtual network interface 820 can include endpoints 822 and 824 that form a virtual wire from VM2 808 to subnet bridge 826. Endpoints 816 and 818 may also be virtual network devices that form a virtual wire from VM1 806 and subnet bridge 828. Any suitable virtual machine (e.g., VM1 806) may participate in multiple subnets and may be assigned multiple IP addresses corresponding to the subnets in which it participates.

In some embodiments, endpoints of virtual network interfaces may be configured in different networking namespaces. For example, endpoint 812 may be in a first networking namespace associated with the PVN data plane 802, while endpoint 814 may be in a second networking namespace associated with the orchestration module 804. The first networking namespace may be the networking namespace of the host operating system, while the second networking namespace may be a namespace of a container hosting the orchestration module 804. An endpoint in a particular networking namespace may be configured as a device of that namespace, with addresses and routing information corresponding to that namespace. For example, endpoint 812 may be a virtual network device (e.g., a virtual Ethernet device) in the host operating system namespace, while endpoint 814 may be a virtual network device of the orchestration module 804 namespace. In this way, the virtual network interface 810 may provide an interface for virtual machine 806 to a private virtual network provided by the PVN data plane 802.

In some embodiments, orchestration module 804 may implement one or more subnets in conjunction with one or more PVNs. For example, a first PVN may be associated with a first subnet, while a second PVN may be associated with a second subnet. A PVN may include one or more VNICs (e.g., virtual NIC(s) 506 of FIG. 5); the subnet bridge for the PVN may bridge all the VNICs of the PVN. The orchestration module 804 may include one or more subnet bridges (e.g., subnet bridge 826, subnet bridge 828, etc.) corresponding to the PVNs within the distributed computing cluster. As a particular example in FIG. 8, VM1 806 may be associated with two PVNs, and can interface with a first PVN via endpoint 812 (of virtual network interface 810) and a second PVN via endpoint 816. Similarly, VM2 808 may be associated with the first PVN and can interface with the first PVN via endpoint 822 (of virtual network interface 820). The corresponding network devices in the namespace of orchestration module 804 (endpoint 814, endpoint 824) may then be connected by subnet bridge 826 for the first PVN. Subnet bridge 828 may connect to endpoint 818, which is the interface corresponding to VM1's 806 association with the second PVN. Although described with respect to two PVNs, numerous other configurations and arrangements of PVNs, VMs, and VNICs are possible.

Orchestration module 804 may also include dynamic host control protocol (DHCP) services 829, 831 for subnet bridges 826 and 828, respectively. The DHCP services 829, 831 may provide dynamic addressing for devices associated with subnet bridges 826 and 828, including endpoints 814, 818, and 824 and interfaces 830 and 832.

To connect the one or more PVNs to other networks of the distributed computing cluster (e.g., network 848, substrate network 850), the orchestration module 804 can include additional network interfaces 830 and 832. Interfaces 830 and 832 may be virtual network devices (e.g., virtual Ethernet devices) within the networking namespace of the orchestration module 804. For instance, interface 830 may be a virtual network device configured to connect to network 848 via the substrate bridge 844 and gateway module 834. Similarly, interface 832 may be a virtual network device (e.g., a virtual Ethernet device) configured to connect to substrate network 850 (and example of the substrate network 504 of FIG. 5). As a particular example, data may be sent from VM1 806 to a client device connected to the edge device via network 848. The data may be sent from VM1 806 to PVN data plane 802 via virtual network interface 810, forwarded by subnet bridge 826 to interface 830, to gateway module 834 via substrate bridge 844, and out to the client device on network 848 via physical NIC1.

Substrate bridge 844 may be configured to connect one or more services 846 with containers, virtual machines, and other services executing on edge device 800. Services 846 may be examples of service(s) 502 of FIG. 5, including a PVN control plane, an identity management service, a block storage management service, and the like. Other services connected via the substrate bridge 844 may be services within the PVN data plane 802, including gateway module 834, metadata service 836, DNS 838, NTP 840, and other SNIC service(s) 842. Gateway 834 may be an internet gateway for a public internet, public network, client network, or other network (e.g., network 848) distinguished from the substrate network 850 that may carry intra-node traffic (e.g., between edge device 800 and other edge devices) within a distributed computing cluster. Metadata service 836 may provide configuration data (e.g., initialization scripts, user-defined configuration data, etc.) to all VMs within the edge device 800. The configuration data provided by metadata service 836 may be used when starting a VM on the edge device 800 (e.g., by providing the configuration of a Linux image to execute on the VM). The DNS 838 may provide domain name resolution to all VMs within the edge device 800. The NTP 840 may provide time synchronization to all VMs within the edge device 800.

As described briefly above, a virtual smart NIC may provide additional services to enhance the networking functionality of the edge device. SNIC service(s) 842 can include source/destination checking, security policies (e.g., security groups), metric tracking, and throttling. For example, source/destination checking may be used to ensure that sources/destinations within one or more PVNs are the sources/targets of network traffic, to prevent IP address spoofing. As another example, network security groups may provide a virtual firewall for resources (e.g., VMs) within a PVN, such that some, any, or all VNICs within the PVN may be grouped under a particular set of security rules. In addition, the security service may provide a virtual firewall that encompasses all VNICs within a subnet (e.g., a security list). As a further example, a throttling service may provide throttling or other similar restrictions or flow control on network traffic destined for resources within one or more PVNs.

Figure 9:
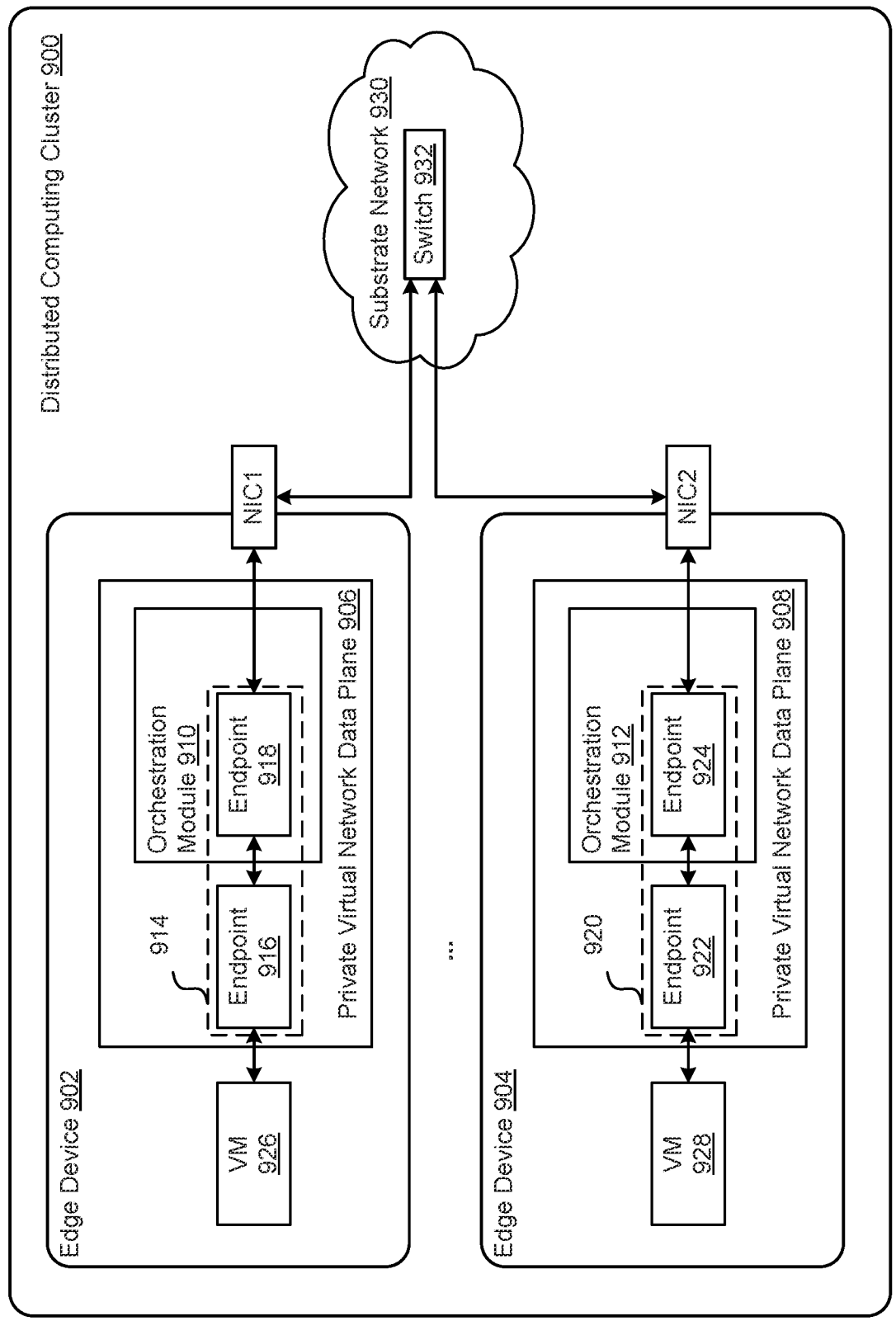
FIG. 9 is a block diagram of an example architecture of a distributed computing cluster with a plurality of edge devices configured to enable network communications using instances of a private virtual network data plane, according to at least one embodiment.

FIG. 9 is a block diagram of an example architecture of a distributed computing cluster 900 with a plurality of edge devices 902 and 904 configured to enable network communications using instances of a private virtual network data plane. The edge devices 902 and 904 may be examples of any of the edge devices described herein, including edge device 500 of FIG. 5 and edge device 800 of FIG. 8. Similarly, the distributed computing cluster 900 may be an example of distributed computing cluster 600 of FIG. 6. Edge device 902 may host PVN data plane 906, while edge device 904 hosts PVN data plane 908. The PVN data planes 906 and 908 may be examples of PVN data plane 802 of FIG. 8. Edge device 902 may also host VM 926 while edge device 904 may host VM 928. VMs 926 and 928 may be examples of other virtual machines described herein, including VM1 806 and VM2 808 of FIG. 8.

In some embodiments, a first VM 926 executing on edge device 902 may send and/or receive data from a second VM 928 executing on edge device 904. For example, VM 926 and VM 928 may be associated with the same PVN that is distributed across the distributed computing cluster 900. To send data to VM 928, VM 926 may send data via PVN data plane 906. The VM 926 may be communicatively connected to a virtual network interface 914. Virtual network interface 914 can include endpoint 916 and endpoint 918. Endpoints 916 and 918 may be similar to endpoints 812 and 814 of FIG. 8 and may be virtual network devices (e.g., virtual Ethernet devices) such that endpoints 916 and 918 form a virtual network wire. Endpoint 916 may be associated with a first networking namespace, which may be the networking namespace of the host operating system of edge device 902. Endpoint 918 may be associated with a second networking namespace of the orchestration module 910.

Similarly, VM 928 may be communicatively connected to virtual network interface 920. Virtual network interfaces 914 and 920 may be examples of virtual network interfaces 810 and 820 of FIG. 8. Virtual network interface 920 can include endpoints 922 and 924, which may be associated with network namespaces of the host operating system of edge device 904 and orchestration module 912, respectively.

Edge device 902 and 904 may be connected by a switch 932 as part of a substrate network 930 (an example of substrate network 504 of FIG. 5). The substrate network 930 can connect all edge devices within the distributed computing cluster 900. In some embodiments, substrate network traffic may be encrypted (e.g., via MACsec) before being sent or received at physical NICs (e.g., NIC1, NIC2).

VM 926 may send a data packet to VM 928 by sending the data packet to endpoint 916. The data packet will be received by orchestration module 910 at endpoint 918. The orchestration module 910 may then forward the data packet to edge device 904. The data packet may be sent to switch 932 via NIC1, where it will be routed to NIC2 at edge device 904. Orchestration module 912 may then route the packet according to the defined networking routing tables for the PVN, so that the data packet may be sent to VM 928 via virtual network interface 920.

Figure 10:
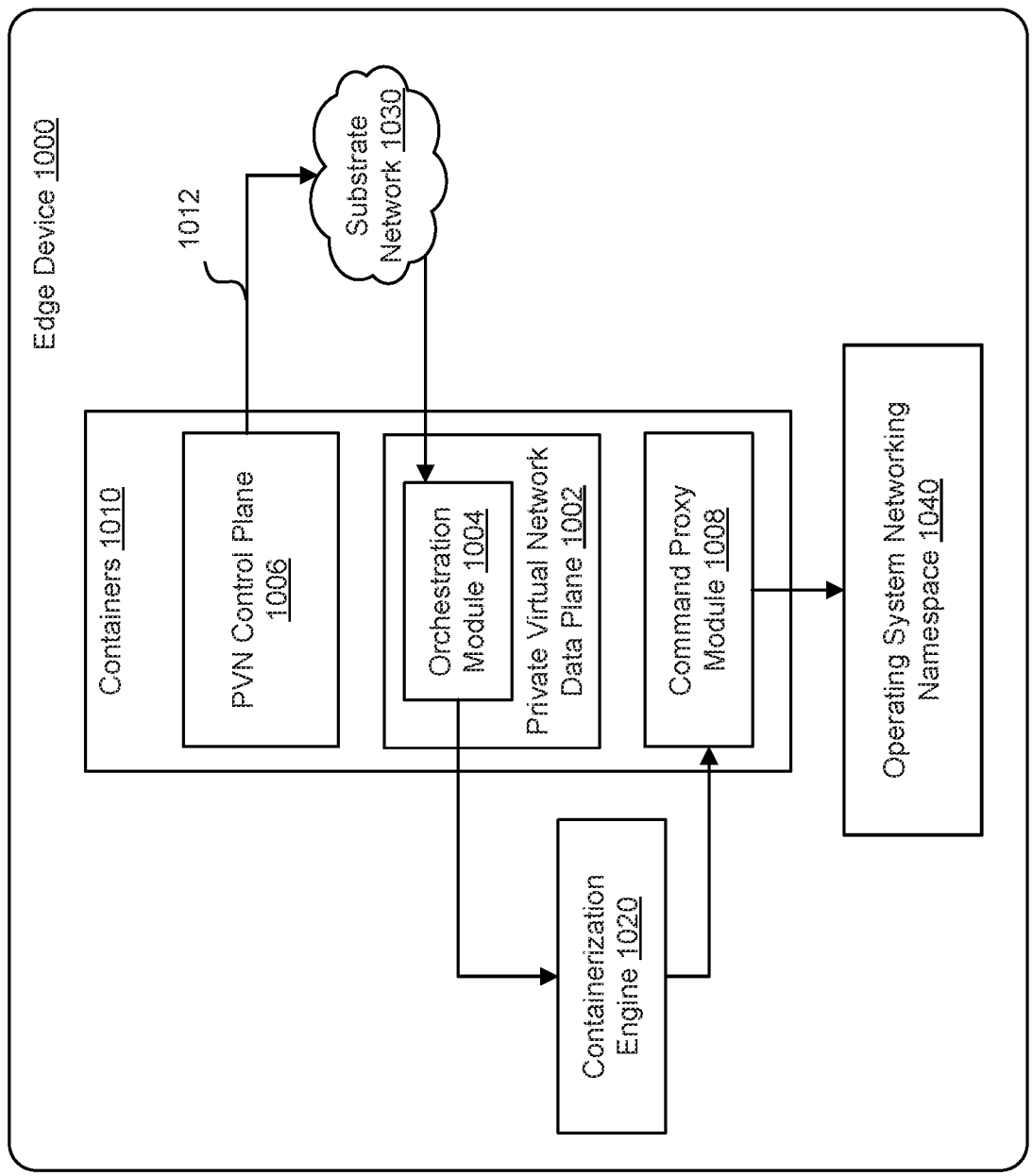
FIG. 10 is a block diagram depicting an edge device hosting a command proxy module to enable namespace operations at the host device operating system, according to at least one embodiment.

FIG. 10 is a block diagram depicting an edge device 1000 hosting a command proxy module 1008 to enable namespace operations at the host device operating system. The edge device 1000 may be similar to other edge devices described herein, including edge device 800 of FIG. 8, edge device 500 of FIG. 5, and edge devices 902 and 904 of FIG. 9. Similarly, substrate network 1030 may be an example of other substrate networks described herein (e.g., substrate network 930 of FIG. 9), while PVN data plane 1002 and orchestration module 1004 may be examples of PVN data plane 802 and orchestration module 804 of FIG. 8.

As described above with respect to FIG. 8, an edge device (e.g., edge device 1000) may host processes in one or more containers, including processes and modules of a PVN data plane. As depicted in FIG. 10, containers 1010 may include containers for PVN control plane 1006, PVN data plane 1002, orchestration module 1004, and command proxy module 1008. Each container may implement its own networking namespace, which can be a logical copy of host operating system networking namespace 1040. For example, operating system networking namespace 1040 may include the configuration of all physical and virtual networking devices (e.g., NICs, bridges, Ethernet interfaces, ports, etc.) and associated addresses, routing information (e.g., routing tables), protocols, and/or drivers accessible to the host operating system. The networking namespaces for each container may then be configured to include networking devices associated with the container and accessible by the container process. For example, the container hosting orchestration module 1004 may include VNICs, virtual Ethernet devices, VLAN devices, subnet bridges (e.g., subnet bridges 826 and 828 of FIG. 8), as well as associated routing information, DHCP information, NAT and firewall information, and/or other networking components accessible to orchestration module 1004. Thus, the networking namespace of orchestration module 1004 may characterize all the interfaces for one or more PVNs implemented in conjunction with PVN data plane 1002.

In some embodiments, some containers may use the networking namespace of the host operating system (e.g., operating system networking namespace 1040). For example, one endpoint of a virtual network interface (e.g., endpoint 812 of virtual network interface 810 of FIG. 8) may be associated with the operating system networking namespace, while the corresponding endpoint (e.g., endpoint 814) may be associated with a second networking namespace of the orchestration module. To associate an endpoint or other virtual networking device with the networking namespace of the host operating system, the operating system networking namespace 1040 may be modified to include the endpoint. As a non-limiting example, in a Linux environment, a virtual network interface may be added to the operating system networking namespace with the command "ip link add [endpoint 1 name] netns [operating system namespace] type veth peer [endpoint 2 name] netns [orchestration module namespace]." Such a command will add a virtual Ethernet endpoint named "endpoint 1 name" to the networking namespace identified as "operating system namespace," which can correspond to the networking namespace of the host operating system. The command may fail if it is executed without sufficient permissions to modify the "operating system namespace."

For security purposes, an entity (e.g., PVN control plane 1006) responsible for managing network interfaces within the PVN data plane 1002 may not have appropriate permissions to directly modify the operating system networking namespace 1040. To permit the modification of the operating system networking namespace 1040, a command proxy module 1008 may be executed on the edge device 1000 to act as a proxy for PVN control plane 1006.

The command proxy module 1008 may be hosted within a container of containers 1010 executing on edge device 1000. The command proxy module 1008 may be configured with permissions to modify the operating system networking namespace 1040, while PVN control plane 1006 may not be configured with permissions to modify the operating system networking namespace 1040. For example, command proxy module 1008 may be configured with sufficient permissions to execute the command "ip link add . . . " to modify the networking namespace of the host operating system.

To create, update, delete, or otherwise manage a virtual network interface within the PVN data plane 1002, the PVN control plane 1006 can send a request 1012 to PVN data plane 1002. The request 1012 may be a RESTful API call. The request 1012 may be sent to the PVN data plane 1002 via substrate network 1030 (e.g., through a connection supported by substrate bridge 844. The request 1012 can include information for executing one or more networking commands to perform the operation for the virtual network interface, including namespace names, endpoint names, interface type, and the like.

The orchestration module 1004 of the PVN data plane 1002 can use the request 1012 and communicate with containerization engine 1020 to execute a command associated with the request 1012. In some embodiments, the containerization engine 1020 can spawn (e.g., instantiate) the command proxy module 1008 at the time the request 1012 is received by the PVN data plane 1002 and communicated to the containerization engine 1020. Said another way, in some embodiments the command proxy module 1008 may not execute until the request 1012 is sent from PVN control plane 1006 to PVN data plane 1002. For example, upon receiving the request 1012, the orchestration module 1004 can communicate with containerization engine 1020 to have containerization engine 1020 create a container and start (e.g., execute) an image of command proxy module 1008 to perform the command associated with the request 1012. Once the command has been successfully completed, the command proxy module 1008 and its container may be removed from containers 1010. In other embodiments, the command proxy module 1008 may execute concurrently with PVN control plane 1006. Then, the containerization engine 1020 may communicate with command proxy module 1008 to provide the command from PVN data plane 1002.

The container for command proxy module 1008 may be created with elevated privileges. The elevated privileges may allow the command proxy module 1008 to perform operations (e.g., execute commands) with permissions to modify components of the host edge device 1000. For example, the command proxy module 1008 may execute a command to add a virtual network device (e.g., a virtual Ethernet device) to the operating system networking namespace 1040.

Figure 11:
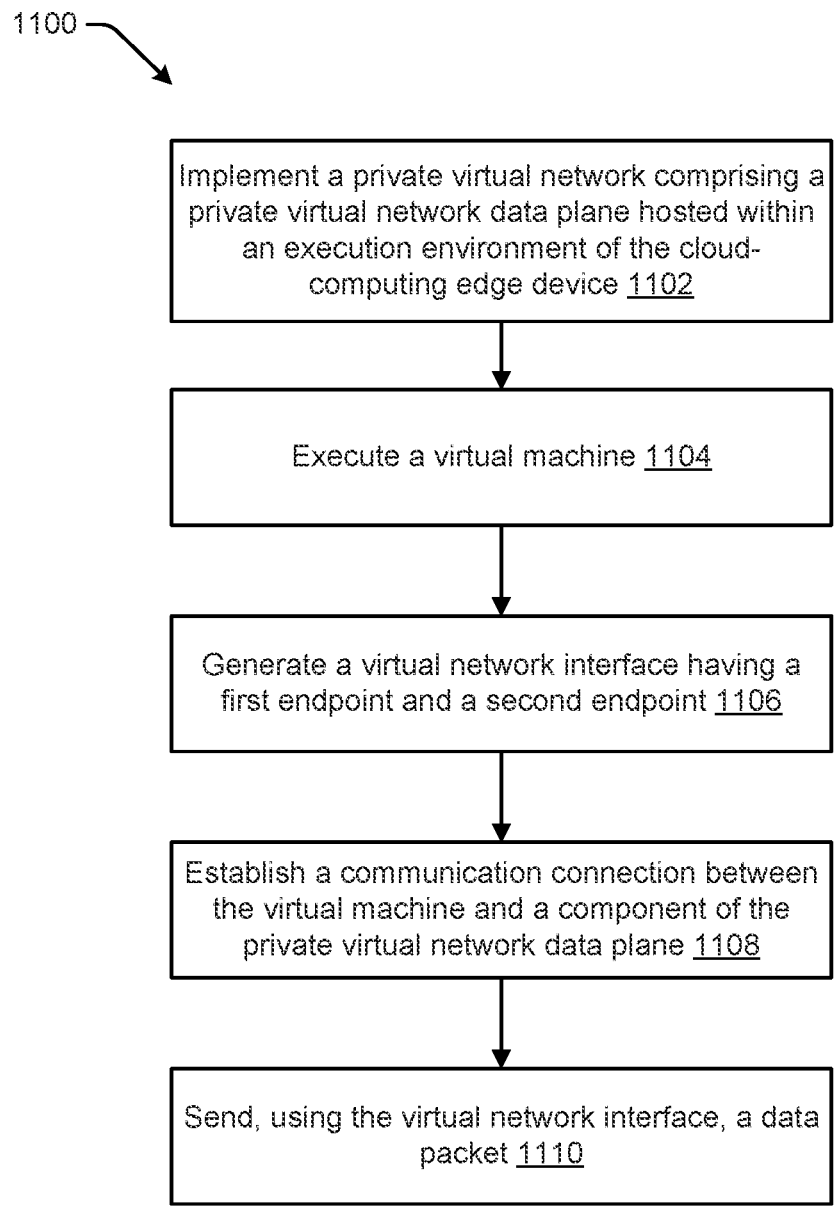
FIG. 11 illustrates an example method for transmitting a data packet through a virtual smart network interface card, according to at least one embodiment.

FIG. 11 illustrates an example method 1100 for transmitting a data packet through a virtual smart network interface card (NIC). The virtual smart NIC may be represented as a data plane for a private virtual network (e.g., the PVN data plane 802 of FIG. 8). The virtual smart NIC may be hosted within an edge device (e.g., edge device 800 of FIG. 8) within a distributed computing cluster (e.g., distributed computing cluster 900 of FIG. 9). The distributed computing cluster can include any suitable number of edge devices, each of which may host its own virtual smart NIC (PVN data plane). The edge devices and distributed computing cluster may be examples of the edge devices and distributed computing clusters described above with respect to FIGS. 1-10. The method 1100 is illustrated as a logical flow diagram, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Some, any, or all of the method 1100 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The method 1100 may begin at block 1102 by implementing a private virtual network (PVN) hosted within an execution environment (e.g., containers 1010 of FIG. 10) of a cloud-computing edge device (e.g., edge device 800 of FIG. 8). The PVN can include a data plane (e.g., PVN data plane 802) that represents a collection of software configured to support the data operations for the PVN. The PVN data plane 802 may also support the data operations of other PVNs implemented on the host edge device (e.g., edge device 800).

At block 1104, the edge device (e.g., edge device 800) may execute a virtual machine (e.g., VM1 806 of FIG. 8). The virtual machine may be managed by a hypervisor (e.g., hypervisor 106 of FIG. 1). The virtual machine may be configured to perform any suitable computational tasks (e.g., compute instances, storage, etc.) on the edge device. The virtual machine may be associated with one or more virtual network interface cards (VNICs) that facilitate connection of the virtual machine to the PVN. For example, each VNIC can have a media access control (MAC) address for layer 2 identification when transmitting data frames.

At block 1106, the edge device (e.g., edge device 800) may generate a virtual network interface (e.g., virtual network interface 810 of FIG. 8). The virtual network interface can include a first endpoint and a second endpoint (e.g., endpoints 812 and 814 of FIG. 8), which may be virtual Ethernet devices (e.g., Linux veth interfaces). The virtual network interface can be hosted within the PVN data plane (e.g., PVN data plane 802).

At block 1108, the edge device (e.g., edge device 800) can establish a communication connection between the virtual machine (e.g., VM1 806) and a component of the PVN data plane (e.g., PVN data plane 802). The communication connection may be established by associating the first endpoint (e.g., endpoint 812) with the virtual machine. Associating the first endpoint with the virtual machine can include exposing the first endpoint as a network interface accessible to the virtual machine. The second endpoint may be associated with an orchestration module (e.g., orchestration module 804) of the PVN data plane. The orchestration module may be configured to provide appropriate network interfaces, subnets, routing tables, firewall, NAT, and/or other networking functionality for the PVN data plane.

At block 1110, the virtual machine (e.g., VM1 806) can send a data packet or data packets (e.g., messages, requests, and other network traffic) using the virtual network interface (e.g., virtual network interface 810). The data packet may be sent through the first endpoint of the virtual network interface and received through the second endpoint at the orchestration module. The orchestration module may then forward the data packet to a destination based on routing information contained in the orchestration module.

In some embodiments, the edge device may execute additional virtual machines, including a second virtual machine (e.g., VM2 808). The first virtual machine (e.g., VM1 806) and the second virtual machine may be part of the same PVN. The edge device can generate a second virtual network interface (e.g., virtual network interface 820) having a third endpoint (e.g., endpoint 822) and a fourth endpoint (e.g., endpoint 824). The second virtual network interface can be hosted within the PVN data plane. The third endpoint can be associated with the second virtual machine, such that the second virtual machine can access the third endpoint to send and/or receive one or more data packets, data frames, or the like. The fourth endpoint can be associated with the orchestration module of the PVN data plane, thus establishing an additional communication connection between the second virtual machine and the orchestration module of the PVN data plane.

The data packet sent from the first virtual machine may be sent to the second virtual machine. In this instance, the orchestration module may forward the data packet according to routing information that identifies the destination of the packet as the second virtual machine in the PVN. In a second example, the data packet may be sent to an external device. In this instance, the PVN data plane may include an internet gateway (e.g., gateway module 834 of FIG. 8). The orchestration module may forward the data packet according to routing information and the internet gateway that identify the external device as the destination for the data packet. The edge device may be communicatively connected to the external device through a public network (e.g., the internet). In a third example, the data packet may be sent to an additional cloud computing edge device (e.g., edge device 904 of FIG. 9). The additional cloud-computing edge device may host an instance of a PVN data plane (e.g., PVN data plane 908 of FIG. 9) and a virtual machine (e.g., VM 928 of FIG. 9). The additional cloud-computing edge device may be connected to the edge device sending the data packet through a substrate network (e.g., substrate network 930 of FIG. 9).

Figure 12:
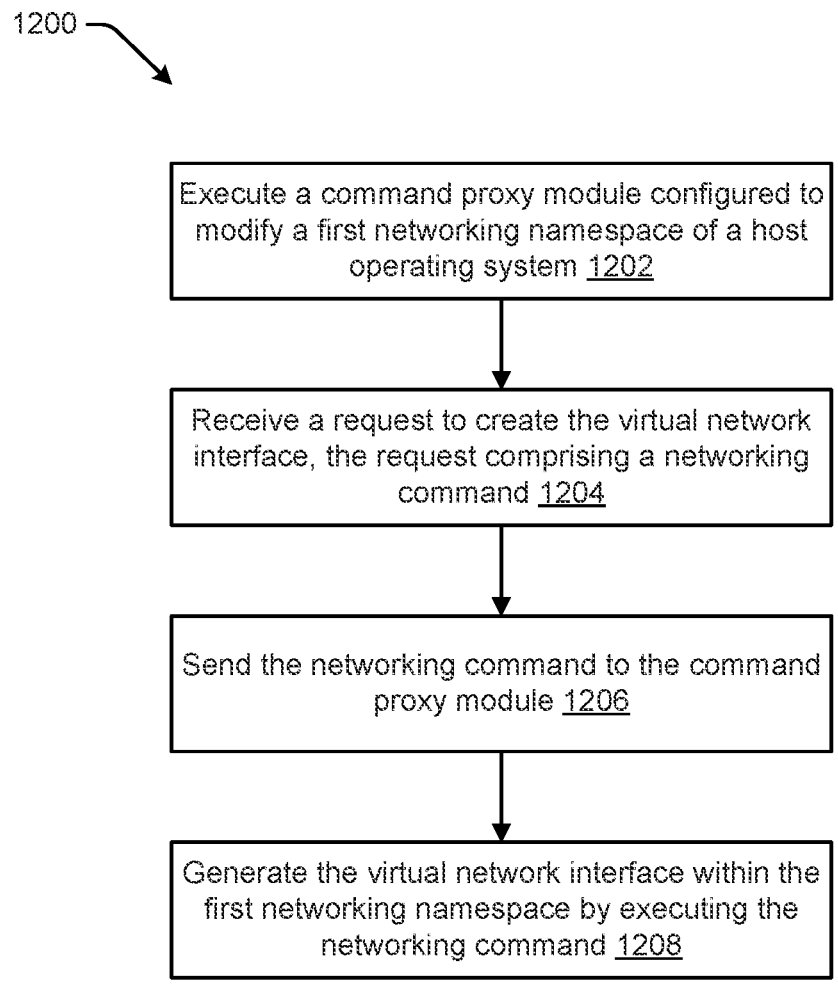
FIG. 12 illustrates an example method for modifying a networking namespace of a host operating system of an edge device via a command proxy module, according to at least one embodiment.

FIG. 12 illustrates an example method 1200 for modifying a networking namespace (e.g., operating system networking namespace 1040 of FIG. 10) of a host operating system of an edge device (e.g., edge device 1000 of FIG. 10) via a command proxy module (e.g., command proxy module 1008), according to at least one embodiment. The edge device may host a PVN data plane (e.g., PVN data plane 1002 of FIG. 10) and a PVN control plane (e.g., PVN control plane 1006 of FIG. 10) in containers (e.g., containers 1010 of FIG. 10) managed by a containerization engine (e.g., containerization engine 1020 of FIG. 10). The configuration of containers within an edge device is described in detail with respect to FIG. 1 above. The containers hosted on the edge device may be communicatively connected over a substrate network (e.g., substrate network 1030 of FIG. 10), which can provide communication channels between a services, containers, and virtual machines hosted on an edge device as well as between a plurality of edge devices (and corresponding services, containers, virtual machines, and other process hosted thereon) in a distributed computing cluster.

At block 1202, the edge device (e.g., edge device 1000) may execute a command proxy module (e.g., command proxy module 1008 of FIG. 10). The command proxy module may be configured to modify the networking namespace of a host operating system (e.g., a first networking namespace). For example, the command proxy module may be executed in a container that is created with elevated privileges for interacting with host operating system.

At block 1204, the PVN data plane can receive a request (e.g., request 1012) to create a first virtual network interface. The request can include a networking command (e.g., "ip link add . . . "). The request may be sent by a control plane (e.g., PVN control plane 1006) for the PVN data plane. The request may be a RESTful API call.

At block 1206, the PVN data plane can send the networking command to the command proxy module. The networking command may be sent via the containerization engine. Finally, at block 1208, the command proxy module can execute the networking command to generate the virtual network interface within the first networking name space of the host operating system. In some embodiments, the networking command may specify that a pair of virtual network devices (e.g., endpoints 812 and 814) are to be created, and that the first endpoint is to be included in the first networking namespace and the second endpoint is to be included in a second networking namespace associated with the orchestration module.

In some embodiments, the operations of block 1202 to execute the command proxy module may occur after receiving the request according to the operations of block 1204. For example, the command proxy module may be started in a container in response to the PVN data plane receiving the request. Upon successful execution of the networking command according to the operations of block 1208, the command proxy module and its container may be removed.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
   implementing, by a cloud-computing edge device, a private virtual network, the private virtual network comprising a private virtual network data plane hosted within an execution environment of the cloud-computing edge device;
   executing, by the cloud-computing edge device, a virtual machine;
   generating, by the cloud-computing edge device, a virtual network interface having a first endpoint and a second endpoint, the virtual network interface being hosted within the private virtual network data plane;
   establishing a communication connection between the virtual machine and a component of the private virtual network data plane based at least in part on associating the first endpoint of the virtual network interface with the virtual machine and associating the second endpoint of the virtual network interface with an orchestration module of the private virtual network data plane; and sending, by the virtual machine and using the virtual network interface, a data packet, the data packet being sent through the first endpoint to the second endpoint.

2. The computer-implemented method of claim 1, wherein the virtual machine comprises a first virtual machine, wherein the virtual network interface comprises a first virtual network interface associated with a first subnet of the private virtual network, and further comprising:

executing, by the cloud-computing edge device, a second virtual machine;

generating, by the cloud-computing edge device, a second virtual network interface having a third endpoint and a fourth endpoint, the second virtual network interface being hosted within the private virtual network data plane and associated with a first subnet of the private virtual network; and establishing an additional communication connection between the second virtual machine and the orchestration module of the private virtual network data plane based at least in part on associating the third endpoint with the second virtual machine and associating the fourth endpoint with the orchestration module.

3. The computer-implemented method of claim 2, wherein sending the data packet comprises sending the data packet from the first virtual machine to the second virtual machine using the first virtual network interface and the second virtual network interface.

4. The computer-implemented method of claim 1, wherein the private virtual network data plane comprises a gateway module, and further comprising forwarding, by the private virtual network data plane using the gateway module, the data packet to an external device, the cloud-computing edge device communicatively connected to the external device through a public network.

5. The computer-implemented method of claim 1, wherein the cloud-computing edge device is one of a plurality of cloud-computing edge devices, and further comprising forwarding, by the orchestration module of the private virtual network data plane, the data packet to an additional cloud-computing edge device of the plurality of cloud-computing edge devices, the cloud-computing edge device communicatively connected to the additional cloud-computing edge device through a substrate network.

6. The computer-implemented method of claim 1, further comprising:

executing, by the cloud-computing edge device, a command proxy module configured to modify a first networking namespace of a host operating system executing on the cloud-computing edge device;

receiving, at the private virtual network data plane, a request to create the virtual network interface, the request comprising a networking command;

sending, by the private virtual network data plane to the command proxy module, the networking command; and generating the virtual network interface within the first networking namespace by executing the networking command.

7. The computer-implemented method of claim 6, wherein the first endpoint is associated with the first networking namespace of the host operating system and the second endpoint is associated with a second networking namespace of the orchestration module.

8. A cloud-computing edge device, comprising:
one or more processors; and
one or more memories storing computer-executable instructions that, when executed with the one or more processors, cause the cloud-computing edge device to:
implement a private virtual network, the private virtual network comprising a private virtual network data plane hosted within an execution environment of the cloud-computing edge device;
execute a virtual machine;
generate a virtual network interface having a first endpoint and a second endpoint, the virtual network interface being hosted within the private virtual network data plane;
establish a communication connection between the virtual machine and a component of the private virtual network data plane based at least in part on associating the first endpoint of the virtual network interface with the virtual machine and associating the second endpoint of the virtual network interface with an orchestration module of the private virtual network data plane; and
send, by the virtual machine and using the virtual network interface, a data packet, the data packet being sent through the first endpoint to the second endpoint.

9. The cloud-computing edge device of claim 8, wherein the virtual machine comprises a first virtual machine, wherein the virtual network interface comprises a first virtual network interface associated with a first subnet of the private virtual network, and storing additional instructions that, when executed with the one or more processors, cause the cloud-computing edge device to further:

execute a second virtual machine;
generate a second virtual network interface having a third endpoint and a fourth endpoint, the second virtual network interface being hosted within the private virtual network data plane and associated with a first subnet of the private virtual network; and
establish an additional communication connection between the second virtual machine and the orchestration module of the private virtual network data plane based at least in part on associating the third endpoint with the second virtual machine and associating the fourth endpoint with the orchestration module.

10. The cloud-computing edge device of claim 9, wherein the data packet is sent from the first virtual machine to the second virtual machine using the first virtual network interface and the second virtual network interface.

11. The cloud-computing edge device of claim 8, wherein the private virtual network data plane comprises a gateway module, and storing additional instructions that, when executed with the one or more processors, cause the cloud-computing edge device to further forward, by the private virtual network data plane using the gateway module, the data packet to an external device, the cloud-computing edge device communicatively connected to the external device through a public network.

12. The cloud-computing edge device of claim 8, wherein the cloud-computing edge device is one of a plurality of cloud-computing edge devices, and storing additional instructions that, when executed with the one or more processors, cause the cloud-computing edge device to further forward, by the orchestration module of the private virtual network data plane, the data packet to an additional cloud-computing edge device of the plurality of cloud-computing edge devices, the cloud-computing edge device communicatively connected to the additional cloud-computing edge device through a substrate network.

13. The cloud-computing edge device of claim 8, storing additional instructions that, when executed with the one or more processors, cause the cloud-computing edge device to further:

execute a command proxy module configured to modify a first networking namespace of a host operating system executing on the cloud-computing edge device;

receive, at the private virtual network data plane, a request to create the virtual network interface, the request comprising a networking command;

send, by the private virtual network data plane to the command proxy module, the networking command; and generate the virtual network interface within the first networking namespace by executing the networking command.

14. The cloud-computing edge device of claim 13, wherein the first endpoint is associated with the first networking namespace of the host operating system and the second endpoint is associated with a second networking namespace of the orchestration module.

15. A computer-readable storage medium comprising executable instructions that, when executed by one or more processors of a cloud-computing edge device, cause the cloud-computing edge device to:

implement a private virtual network, the private virtual network comprising a private virtual network data plane hosted within an execution environment of the cloud-computing edge device;

execute a virtual machine;

generate a virtual network interface having a first endpoint and a second endpoint, the virtual network interface being hosted within the private virtual network data plane;

establish a communication connection between the virtual machine and a component of the private virtual network data plane based at least in part on associating the first endpoint of the virtual network interface with the virtual machine and associating the second endpoint of the virtual network interface with an orchestration module of the private virtual network data plane; and send, by the virtual machine and using the virtual network interface, a data packet, the data packet being sent through the first endpoint to the second endpoint.

16. The computer-readable storage medium of claim 15, wherein the virtual machine comprises a first virtual machine, wherein the virtual network interface comprises a first virtual network interface associated with a first subnet of the private virtual network, and comprising additional instructions that, when executed by the one or more processors, cause the cloud-computing edge device to further:

execute a second virtual machine;

generate a second virtual network interface having a third endpoint and a fourth endpoint, the second virtual network interface being hosted within the private virtual network data plane and associated with a first subnet of the private virtual network; and establish an additional communication connection between the second virtual machine and the orchestration module of the private virtual network data plane based at least in part on associating the third endpoint with the second virtual machine and associating the fourth endpoint with the orchestration module.

17. The computer-readable storage medium of claim 16, wherein the data packet is sent from the first virtual machine to the second virtual machine using the first virtual network interface and the second virtual network interface.

18. The computer-readable storage medium of claim 15, wherein the private virtual network data plane comprises a gateway module, and comprising additional instructions that, when executed by the one or more processors, cause the cloud-computing edge device to further forward, by the private virtual network data plane using the gateway module, the data packet to an external device, the cloud-computing edge device communicatively connected to the external device through a public network.

19. The computer-readable storage medium of claim 15, wherein the cloud-computing edge device is one of a plurality of cloud-computing edge devices, and comprising additional instructions that, when executed with the one or more processors, cause the cloud-computing edge device to further forward, by the orchestration module of the private virtual network data plane, the data packet to an additional cloud-computing edge device of the plurality of cloud-computing edge devices, the cloud-computing edge device communicatively connected to the additional cloud-computing edge device through a substrate network.

20. The computer-readable storage medium of claim 15, comprising additional instructions that, when executed by the one or more processors, cause the cloud-computing edge device to further:

execute a command proxy module configured to modify a first networking namespace of a host operating system executing on the cloud-computing edge device;

receive, at the private virtual network data plane, a request to create the virtual network interface, the request comprising a networking command;

send, by the private virtual network data plane to the command proxy module, the networking command; and generate the virtual network interface within the first networking namespace by executing the networking command.

* * * * *

UNITED STATES PATENT AND TRADEMARK OFFICE
CERTIFICATE OF CORRECTION

| | | |
|---|---|---|
| PATENT NO. | : 12,081,393 B2 | Page 1 of 1 |
| APPLICATION NO. | : 17/569470 | |
| DATED | : September 3, 2024 | |
| INVENTOR(S) | : Zaicenko et al. | |

It is certified that error appears in the above-identified patent and that said Letters Patent is hereby corrected as shown below:

In the Specification

In Column 22, Line 60, delete "name space" and insert -- namespace --, therefor.

Signed and Sealed this
Seventh Day of January, 2025

Derrick Brent
*Acting Director of the United States Patent and Trademark Office*